US00PP32954P3

(12) United States Plant Patent
Hansen

(10) Patent No.: US PP32,954 P3
(45) Date of Patent: Apr. 6, 2021

(54) ***LAGERSTROEMIA* PLANT NAMED 'DARK ROAST'**

(50) Latin Name: ***Lagerstroemia* (L.) hybrid**
Varietal Denomination: Dark Roast

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/350,861

(22) Filed: Jan. 24, 2019

(65) Prior Publication Data

US 2020/0245518 P1 Jul. 30, 2020

(51) Int. Cl.
*A01H 5/02* (2018.01)
*A01H 6/00* (2018.01)

(52) U.S. Cl.
USPC ..... Plt./252
CPC ..... *A01H 6/00* (2018.05); *A01H 5/02* (2013.01)

(58) Field of Classification Search
USPC ..... Plt./252
CPC ..... A01H 6/00; A01H 5/02
See application file for complete search history.

*Primary Examiner* — Keith O. Robinson

(57) ABSTRACT

The new and distinct crape myrtle plant named *Lagerstroemia* 'Dark Roast' has a dense, short, compact, broadly-rounded habit, is ground hardy to at least USDA zone 6, has semi-glossy, mahogany-colored foliage becoming deep green at flowering time. The flowers arise from shiny, deep-red buds, are lightly fragrant, covering the shrub with their bright fuchsia-pink color. The new plant resists leaf spot and powdery mildew and is useful in the landscape as a specimen, en masse, or as a container plant.

1 Drawing Sheet

Botanical classification: *Lagerstroemia* (L.) hybrid.
Variety denomination: 'Dark Roast'.

STATEMENT REGARDING PRIOR DISCLOSURES UNDER 37 CFR 1.77(B)(6)

The first public disclosure of the claimed plant, in the form of a photograph and brief description was on a website operated by Walters Gardens, Inc. on Feb. 1, 2018. After that, on Mar. 12, 2018 the claimed plant was sold by Walters Gardens, Inc., who obtained the plant and all information relating thereto, from the inventor. No plants of *Lagerstroemia* 'Dark Roast' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Lagerstroemia* plant, commonly known as Crape Myrtle, and hereinafter referred to by the cultivar name 'Dark Roast' or the "new plant." 'Dark Roast' is grown primarily as an ornamental for landscape use and for use as a potted plant and is the result of an ongoing breeding program to produce new and improved garden worthy plants for the ornamental market. The new plant was the result of pollination in an isolation block in August of 2012 at a wholesale perennial nursery in Zeeland, Mich., USA using the unreleased proprietary hybrid H10-11-22 (not patented) as the seed or female parent and the male or pollen parent is a sibling named with only with the breeder code H10-11-23 (not patented). The new plant was given the breeder code 12-30-1.

*Lagerstroemia* 'Dark Roast' was initially asexually propagated by stem cuttings at a wholesale perennial nursery in Zeeland, Mich., USA in 2014. The resultant plants from successive generations have demonstrated that the new plant has remained stable and true to type in multiple and successive generations of asexual propagation.

SUMMARY OF THE INVENTION

Plants of the new cultivar 'Dark Roast' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Dark Roast'. Among the characteristics in combination which distinguish 'Dark Roast' as a new and distinct cultivar, unique from all other cultivars known to the inventor are:

1. Dense, short, compact, broadly-rounded growth habit;
2. Semi-glossy foliage of mahogany develop to deep green at flowering period;
3. Heavily-branched reddish-brown colored stems;
4. Bright fuchsia-pink flowers open from deep red buds on new growth to cover the shrub;
5. Resistance to *Cercospora* leaf spot and *Erisphe* powdery mildew;
6. Ground hardy to at least USDA hardiness zone 6.

The most similar cultivars known to the inventor include: 'Spiced Plum' U.S. Plant Pat. No. 29,478, 'Whit VI' U.S. Plant Pat. No. 14,438, 'Cool Beans' U.S. Plant Pat. No.

29,940, 'Sweet Macchiato' U.S. Plant Pat. No. 28,759, and the three copending cultivars 'Chai Berry' U.S. Plant patent application Ser. No. 16/350,860, and 'Lava Java' U.S. Plant patent application Ser. No. 16/350,862. 'Spiced Plum' blooms about a week later with flowers that are more raspberry purple. 'Whit VI' is much larger in habit and has flowers of a different color. 'Cool Beans' has slightly larger habit and the flower color is a different pink hue. 'Sweet Macchiato' is slightly larger in habit and the flower color is of a more lavender pink hue and less bright fuchsia-pink. 'Chai Berry' is slightly taller in habit and the flower color is a different hue of rosy pink. 'Lava Java' is slightly taller in habit and the flowers are a deeper reddish hue. The female parent is slightly taller and broader in habit with more dense branching, and the flower color is a coral pink hue. The male parent is shorter in habit, the leaves more green and less mahogany and the flower not as fuchsia.

BRIEF DESCRIPTION OF THE DRAWINGS

The accompanying color photographs illustrate the flower and foliage characteristics and the overall appearance of a five-year-old plant of 'Dark Roast', growing in a full-sun trial garden in Zeeland, Mich., showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
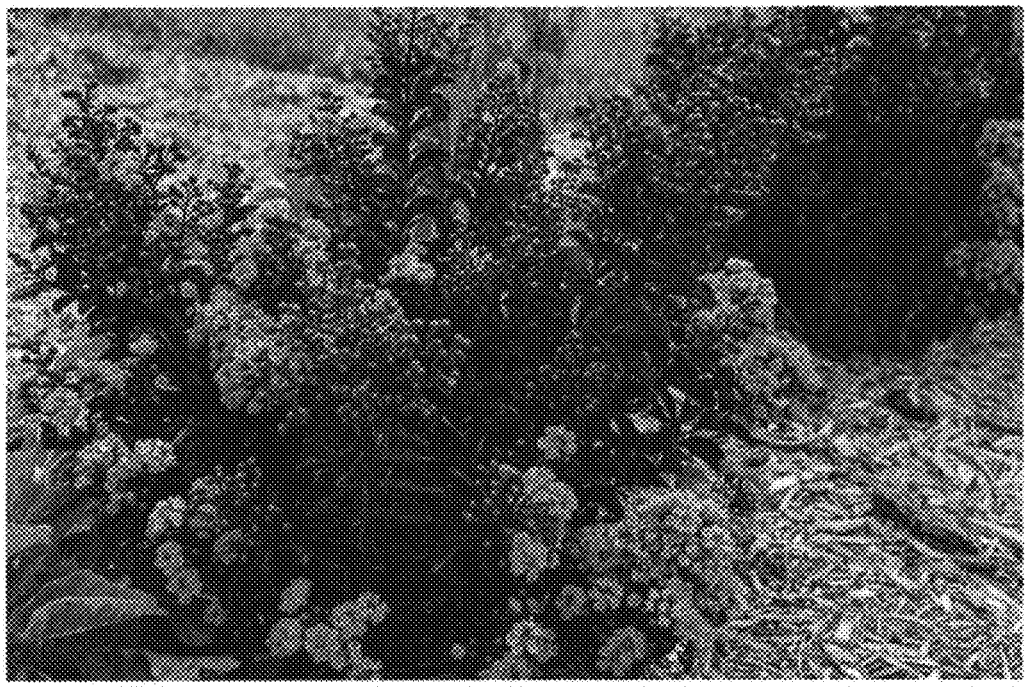
FIG. 1 shows a plant in a full-sun trial garden in late summer peak flowering.
Figure 2:
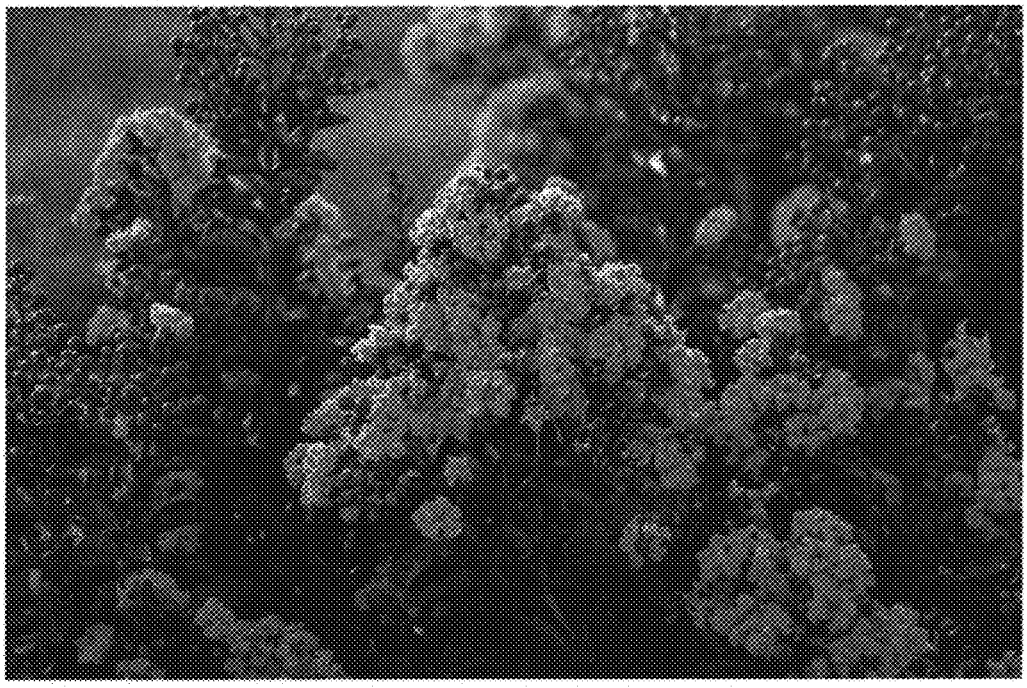
FIG. 2 shows a close-up for the flowers and buds.

The following color references are based on the 2015 edition of The Royal Horticultural Society Colour Chart except where common dictionary terms are used. The following observations and size descriptions are of approximately five-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* (L.) hybrid;

Parentage: Female, or seed parent H10-11-22; the male, or pollen parent is H10-11-23;

Propagation: Terminal softwood stem cuttings;

Time to initiate roots: About three weeks;

Growth rate: Moderate; finishing from a 65 mm liner in a 3.7 liter container in about 10 to 14 weeks during the summer season;

Plant description: Deciduous, woody, narrow, compact flowering shrub; about six mainly upright to outward primary stems; freely branched;

Root description: Fine, numerous, fibrous, well-branched;

Plant habit: About 53.0 cm high from the soil level to the top of the inflorescences; about 68.0 cm wide with no pinching, pruning or plant growth regulators;

Stems: About twelve per plant; to about 35.0 cm long and about 12.0 mm diameter at base; young stems cylindrical with four longitudinal carinae, along line on either side of petioles; basal stems cylindrical with slightly exfoliating bark; highly branched with about 12 to 20 alternate branches held at about 45 degree angle above horizontal; branches to about 25.0 cm long and 4.0 mm diameter at base;

Stem color: Woody basal portion variable with nearest RHS 165A and RHS 166C; young developing stems striated with blend of RHS 199B and RHS 177B and darker portions nearest RHS 166A;

Node: About 20 to 25 per main stem; internode length average about 2.2 cm in main stems;

Node color: Same as surrounding stem, striated with blend of RHS 199B and RHS 177B;

Foliage description: Sub-opposite to alternate; simple; ovate; margin ciliolate, slightly involute; acute apex; aequilateral, rounded to attenuate base; to about 5.5 cm long and 3.5 cm wide, average about 4.2 cm long and 2.9 cm wide; adaxial and abaxial glabrous and lustrous;

Abaxial leaf color: Young emerging adaxial RHS 187C, abaxial nearest RHS 184A; mature adaxial nearest RHS 139A with frequent light blush of nearest RHS N187A around perimeter, abaxial nearest RHS NN137B;

Veins: Pinnate, puberulent adaxial and abaxial;

Vein color: Young emerging adaxial nearest RHS 187C, abaxial nearest RHS 187C; mature adaxial midrib nearest RHS 187A, secondary veins nearest RHS 138A; mature abaxial midrib nearest RHS 184A, secondary veins nearest RHS 187B;

Petiole: Short, typically 1.0 mm long and 1.0 mm wide; color nearest RHS N187A both adaxial and abaxial of mature and young leaves;

Inflorescence: Panicle; terminal branched panicles up to about 400 flowers; average about 250 flowers; up to about 26.0 cm long and about 23.0 cm across; beginning mid-July and continuing for about seven weeks;

Buds: Globose to ellipsoidal with rounded to slightly apiculate apex and rounded base; carinate; lustrous; glabrous; about 7.0 mm long and about 6.0 mm diameter one day prior to opening; sutures weakly prominent;

Bud color: Exposed petals nearest RHS NN74C; sun exposed dorsal portion nearest RHS 187B, ventral portion nearest RHS 179A with undertones of nearest RHS 146D, with carina same as surrounding portion, sun exposed dorsal portion nearest RHS 187B, ventral portion nearest RHS 179A with undertones of nearest RHS 146D;

Flowers: Perfect; regular; actinomorphic; terminal panicle; individually about 27.0 mm across and about 15.0 mm long to tip of exserted anthers, corolla to about 14.0 mm long; lasting about two days;

Flower fragrance: Faintly sweet;

Peduncle: Cylindrical with four longitudinal carinae in proximal portion and cylindrical in distal portion; about 4.5 mm diameter at base below lowest flowering branch, to about 26.0 cm long;

Peduncle color: Variable with position; proximal variable with nearest RHS 200A and between RHS 177A and RHS 177B, and distal portion striated with nearest RHS 185A and nearest RHS 187B;

Pedicel: Cylindrical; glabrous; lustrous; about 4.0 mm long and 1.0 mm diameter;

Pedicel color: Nearest RHS 187B;

Calyx: Fused into hypanthium; 7.0 mm long and 9.0 mm across;

Sepals: Fused in about the basal 5.0 mm; acute apex, entire margin; glabrous and lustrous both adaxial and abaxial; about 9.0 mm long and individually and about 3.5 mm wide at fusion point;

Sepal color: Adaxial basal 3.0 mm nearest RHS 157D with middle between RSH 182C and RHS 186C, apical portion between RHS 195D and RHS 197D with light blush nearest RHS 182C; abaxial variable nearest RHS 187A and RHS 183C;

Petals: Six; stalked; glabrous; blade ruffled or crisped; margin crisped; blade with rounded apex and auriculate base, to about 15.0 mm across and 9.0 mm long; claw base or stalk adnate to calyx, to about 5.0 mm long and 1.0 mm diameter; overall about 14.0 mm long;

Petal color: Blade adaxial and abaxial nearest RHS 64B; claw nearest RHS 64B;

Androecium:

*Stamens*.—Typically about 36; six longer and about 30 shorter.

*Filaments*.—Shorter stamens to about 10.0 mm long and about 0.2 mm diameter, curved to twisted; longer filaments about 15.0 mm long and about 0.3 mm diameter; color of shorter filaments between RHS 56B and RHS 54D; color longer filaments nearest RHS 57B.

*Anthers*.—Flattened ellipsoid; more developed on longer stamens to about 1.7 mm long and 1.0 mm across, on shorter stamens about 1.2 mm long and about 0.7 mm across; color nearest RHS 12C.

*Pollen*.—Abundant on longer stamens; color nearest RHS 13A.

Gynoecium: One; about 14.0 mm long;

*Style*.—Cylindrical; glabrous; about 11.5 mm long and 0.5 mm diameter; color nearest RHS 181B.

*Stigma*.—Globose; about 0.5 mm diameter; color nearest RHS 187A.

*Ovary*.—Superior; globose; lustrous; about 2.0 mm tall and 2.0 mm diameter; color nearest RHS 150D.

Fruit: Globose; dehiscent, loculicidal, penta-valved capsule; about 7.0 mm across and 9.0 mm long; immature color nearest RHS 146B, mature nearest RHS 199C;

Seed: Typically 12 to 24 per fruit; winged; to 6.5 mm long and 3.0 mm across and 1.0 mm thick at embryo; color between RHS 199D and RHS 161A;

Disease resistance: *Lagerstroemia* 'Dark Roast' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

It is claimed:

1. A new and distinct cultivar of crape myrtle plant named *Lagerstroemia* 'Dark Roast' essentially as herein illustrated and described.

* * * * *